United States Patent [19]

Schmid et al.

[11] Patent Number: 4,822,874
[45] Date of Patent: Apr. 18, 1989

[54] PROCESS FOR PREPARING CYCLOOCTAAMYLOSE

[75] Inventors: Gerhard Schmid; Hans-Jürgen Eberle, both of Munich, Fed. Rep. of Germany

[73] Assignee: Consortium fur Elektrochemische Industrie, GmbH, Munich, Fed. Rep. of Germany

[21] Appl. No.: 183,661

[22] Filed: Apr. 19, 1988

[30] Foreign Application Priority Data

May 14, 1987 [DE] Fed. Rep. of Germany ....... 3716181

[51] Int. Cl.$^4$ .............................................. C08B 37/16
[52] U.S. Cl. ..................................... 536/102; 536/103
[58] Field of Search ......................................... 536/102

[56] References Cited

U.S. PATENT DOCUMENTS 3,318,732 5/1967 French et al. ...................... 536/102

FOREIGN PATENT DOCUMENTS 2151647 7/1985 United Kingdom .

OTHER PUBLICATIONS

CA 104:128250q, "Increasing y-Cyclodextrin Yield", Sato et al, Nov. 12, 1985.

Primary Examiner—John Kight
Assistant Examiner—Frederick Krass
Attorney, Agent, or Firm—Collard, Roe & Galgano

[57] ABSTRACT

A process for preparing cyclooctaamylose by enzymatic cleavage of an aqueous preparation of starch in the presence of a complexing agent is disclosed. As a selective complexing agent for cyclooctaamylose, a compound of the formula I is employed.

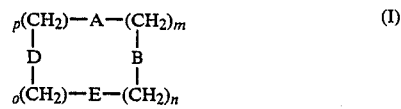

in which A, B, D and E, independently of one another, represent

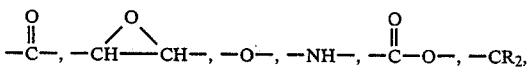

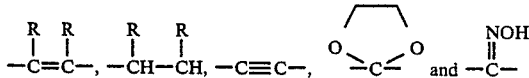

(R=hydrogen, alkyl, hydroxyl, alkoxy or carboxyl radical), and m, n, o and p are within the limits 0 to 20, with the proviso that the number of atoms forming the ring is within the limits from 13 to 24. The compounds prepared by the process of the invention are useful in the medicaments sector, in crop protection and cosmetics, or in the foodstuffs industry.

9 Claims, No Drawings

PROCESS FOR PREPARING CYCLOOCTAAMYLOSE

The present invention relates to a process for preparing cyclooctaamylose by enzymatic cleavage of starch in the presence of a complexing agent.

Cyclooctaamylose is relatively readily water-soluble and has a hydrophobic torus of diameter $10 \times 10^{-10}$ m, in which guest molecules can be included. Due to these properties, cyclooctaamylose is a proven substance for use, inter alia, in the medicaments sector, in the areas of crop protection and cosmetics, or in the foodstuffs industry.

According to DE No. 3,317,064 A1, the state of the art is to separate cyclooctaamylose from starch hydrolysates by precipitation using bromobenzene. Disadvantageously, the complexing agent bromobenzene is not selective for cyclooctaamylose, but instead cycloheptaamylose, which can only be separated by complicated methods, is also precipitated at the same time.

In DE No. 3,446,080 A1 and in the corresponding GB No. 2,151,647 A, phenol and benzene derivatives, to which complexing agents for cyclohexaamylose are simultaneously added, are mentioned as complexing agents for cyclooctaamylose. Separation of cyclooctaamylose, cycloheptaamylose and cyclohexaamylose is also necessary in this case.

Chemical Abstracts 104:128250q, in which Japanese Published Specification JP No. 60-227,693 is cited, describes tetracyclic or pentacyclic triterpenoids as complexing agents in the preparation of cyclooctaamylose.

Accordingly, it is an object of the present invention to provide a process for preparing cyclooctaamylose in high purity; the process providing improved yields while, at the same time, simplifying the isolation of cyclooctaamylose.

The foregoing and related objects are accomplished by the present invention which provides a process for preparing cyclooctaamylose by enzymatic cleavage of an aqueous preparation of starch in the presence of a complexing agent, wherein, as a selective complexing agent for cyclooctaamylose, compounds of the formula I

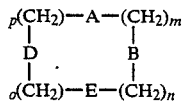

wherein A, B, D and E, independently of one another, represent

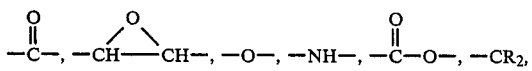

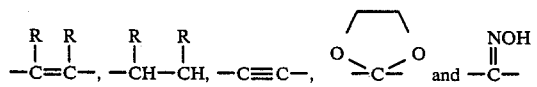

(R = a hydrogen, alkyl, hydroxyl, alkoxy or carboxyl radical) and m, n, o and p are within the limits 0 to 20, with the proviso that the number of atoms forming the ring is within the limits from 13 to 24, are employed.

Examples of radicals R are hydrogen, methyl, ethyl, n-propyl, iso-propyl, n-butyl, sec.-butyl, tert.-butyl, hydroxyl, methoxy, ethoxy and acetoxy radicals. The hydrogen and methyl radicals are preferred, in particular due to their ready accessibility.

Examples of compounds of the formula I are:

(a) macrocyclic unsaturated hydrocarbons, such as cyclotetradeca-1,8-diene, cyclopentadeca-1,8-diene, cyclohexadeca-1,9-diene, cyclohexa-1,5,9,13-tetraene, 1,5,9,13-tetramethylcyclohexadeca-1,5,9,13-tetraene, cyclotetracosa-1,9,17-triene, cyclohexadeca-1,9-diyne and the monoepoxides and polyepoxides thererof, such as 15-oxabicyclo[12.1.0]pentadec-7-ene, 8,16dioxatricyclo[13.1.0.0^{7,9}]hexadecane, 17-oxabicyclo[14.1.0]heptadec-8-ene, 9,18-dioxatricyclo[15.1.0.0^{8,10}]octadecane and 17-oxabicyclo[14.1.0]heptadeca-4,8,12-triene;

(b) macrocyclic ketones or polyketones and acetals, such as cyclotridecanone, cyclotetradec-7-en-1-one, cycloheptadec-9-en1-one, cyclohexadec-8-yn-1-one, cyclotetracosane-1,8,16-trione, cyclotetracosane-1,8,17-trione, 2-methylcyclotridecan-1-one, 3-methylcyclopentadecan-1-one, 17,20-dioxaspiro[15,4]cosane and 1,1-diethoxycyclohexadec-8-ene;

(c) macrocyclic alcohols, such as cyclotetradec-7-en-1-ol, cyclohexadecane-1,8-diol, cyclohexadecane-1,9-diol and cyclohexadeca-5,9,13-trien-1-ol;

(d) macrocyclic alkoxy or carboxyl compounds, such as 1-acetoxycyclohexadec-8-ene, 1-methoxycyclohexadec-8-ene and 1,2-dimethoxycyclohexadec-8-ene;

(e) macrocyclic oxaoxo compounds, such as 2,5-dioxa-1,6-dioxocyclotetradecane, 2,5-dioxa-1,6-dioxocyclohexadecane, 2,5-dioxa-1,6-dioxocycloheptadecane, 2,5-dioxa-1,6-dioxocycloeicosane, 3-methyl-2,5-dioxa-1,6-dioxocyclohexadecane, 2,8-dioxa-1-oxo-cycloheptadecane and 2,7-dioxa-1-oxo-cycloheptadecane;

(f) macrocyclic hydroxyimino compounds, such as 2-oxa-1-oxo6-hydroxyiminocyclohexadecane, 1-hydroxyiminocyclotridecane and 1-hydroxyiminocyclohexadec-8-ene; and (g) macrocyclic monoaza and oligoaza compounds, such as 2-aza-1-oxocyclotridecane, 2,8-diaza-1,9-dioxocyclohexadecane and 2-aza-1-oxocyclotetradec-7-ene.

Compounds of the formula I in which the number of atoms forming the ring is within the limits 13 to 18 are preferably used. These are, in particular, cyclotridecanone, cyclotetradecanone, cyclotetradec-7-en-1-one, 15-oxabicyclo[12.1.0]-pentadec-7-ene, 8,16-dioxatricyclo[13.1.0.0^{7,9}]hexadecane, cyclotetradecane-1,8-dione, cyclopentadec-8-en-1-one, cyclopentadecane-1,8-dione, 16-oxabicyclo[13.1.0]hexadec-6-ene, 8,17-dioxatricyclo[14.1.0.0^{7,9}] heptadecane, cyclohexadec-8-en-1-one, cyclohexadecane-1,9-dione, cyclohexadecane-1,8-dione, cyclohexadeca-1,9-diene, 17-oxabicyclo[14.1.0]cycloheptadec-8-ene, 9,18-dioxatricyclo[15.1.0.0^{8,10}]cyclooctadecane, cycloheptadec-9-en-1-one, cycloheptane-1,9-dione, 18-oxabicyclo-[15.1.0]cyclooctadec-8-ene, 2,5-dioxa-1,6-dioxocyclohexadecane, 2,5-dioxa-1,6-dioxocycloheptadecane, 2,8-dioxa-1-oxocycloheptadecane, 1,7-dioxa-1-oxocycloheptadecane, 2-oxa-1-oxocyclotetradecane, 2-oxa-1-oxocycloheptadecane and 2-oxa-1-oxo-cyclopentadecane.

In principle, any type of starch, including native starch or starch partial hydrolysates, can be employed. Examples are potato starch, maize starch, manioc starch and maltodextrins having a dextrose equivalent < 15.

The aqueous preparations of starch employed can be all aqueous preparations used to date, for enzymatic cleavage of starch. These are, in particular, 4 to 40% by weight aqueous solutions of gelled starch. In the simplest case, they are obtained by boiling appropriate amounts of starch in water. For enzyme stabilization, the preparations mentioned usually contain small amounts of calcium chloride, in particular 5–10 mmole/l.

The known enzyme cyclodextrin glycosyltransferase is now added to the starch preparations mentioned. The source for this enzyme is microorganisms such as *Bacillus macerans* (*Zentr. Bakteriol,* Parasitenk., Dept. II, 14, 722 (1905), *Bacillus stearothermophilus* (U.S. Pat. No. 3,988,206), *Bacillus subtilis* No. 313 (*Agric. Biol. Chem* 50, 8, 2161–2162 (1986), *Bacillus circulans* (U.S. Pat. No. 4,477,568), *Bacillus ohbensis* (JP No. 52-31949), *Bacillus megaterium* (U.S. Pat. No. 3,812,011), *Bacillus* spec. No. 17-1 (U.S. Pat. No. 3,923,598), *Klebsiella pneumoniae* M5 a L (*Arch. Microbiol.* 111, 271 (1977), *Micrococcus luteus* or *Micrococcus varians* (both EP No. 0,017,242).

The enzyme is preferably added in amounts such that the enzyme to starch weight ratio is 1:2000 to 1:50,000, in particular, 1:5000 to 1:20,000.

In the process according to the invention, the complexing agent is preferably added immediately after addition of the enzyme in amounts of, preferably, 1–20% by weight, in particular 8–15% by weight, relative to the weight of the starch employed. The pH of the starch preparation is preferably 4.0 to 11.0, in particular 6.0 to 9.5.

The cleavage reaction is preferably carried out at temperatures of 30°–60° C., in particular 40°–50° C., with stirring; the reaction time preferably being 10–48 hours. The reaction can be monitored, for example, by sampling and chromatographic analysis (HPLC method, *Agric. Biol. Chem.* 49, 4, 1189–1191 (1985).

For work-up, the insoluble cyclooctaamylose complex is removed from the other reaction participants by known methods, for example decanting, filtering or centrifuging. The cyclooctaamylose complex is subsequently again separated into cyclooctaamylose and complexing agent. A suitable method for this purpose is treatment with hot water or steam, the complexing agent being removed from the mixture by steam distillation. A further method includes extracting the water-containing cyclooctaamylose complex with an organic solvent. Examples of such solvents are toluene and cyclohexane.

Up to 48% by weight of cyclooctaamylose, relative to the starch employed, having a purity up to 95%, is obtained.

This cyclooctaamylose is preferably treated in a known manner with glucoamylase in order to remove entrained traces of starch. An organic solvent, such as an alcohol, for example, isopropanol or methanol, or acetone, are preferably added subsequently, whereupon cyclooctaamylose of a purity of 95 to > 99.9% crystallizes out on standing for some time.

Cyclooctaamylose prepared by the process according to the invention is used, inter alia, as a component of plant-protection agents, medicaments, cosmetics and foodstuffs.

The invention will now be described in further detail with reference being made to the following examples. It should, however, be recognized that the following examples are merely illustrative of the scope of the present invention and are not intended to define the limitations thereof.

EXAMPLE 1

20 g of soluble potato starch were suspended in 200 ml of water containing 4 mmole of tris(hydroxymethyl)aminomethane hydrochloride (pH 7.2) and 1 mmole of calcium chloride. The starch was gelled by heating at 95° C. for 25 minutes. After cooling to 50° C., 2 mg of cyclodextrin glycosyltransferase of *Bacillus macerans* and 2.5 g of cyclohexadec-8-en-1-one were added. The batch was incubated at 50° C. for 36 hours with vigorous stirring. By HPLC analysis of an aliquot of the reaction mixture, it was apparent that 46% by weight of the starch employed had been converted into cyclooctaamylose.

The insoluble cyclooctaamylose/cyclohexadec-8-en-1-one complex was removed by centrifuging. The complex was washed twice by taking up in 200 ml of water and subsequent centrifuging. The complex was then taken up in 200 ml of water, and the cyclo hexadec-8-en-1-one was removed by distillation as an azeotrope with water. The resultant cycloamylose solution contained cyclooctaamylose of a purity of 92%.

In order to remove the traces of starch still present, the cycloamylose concentration was set at 40% by weight, and the solution was incubated overnight at 55° C. and pH 5 with 0.5 mg of glucoamylase. The batch was then cooled to room temperature, an equal volume of isopropanol was added, and the mixture was allowed to stand at 4° C. for 4 hours. The precipitate formed was separated off, washed with isopropanol and dried at 60° C. in a vacuum drying cabinet. The yield of cyclooctaamylose was 7.6 g. The purity was > 99%.

EXAMPLE 2

Example 1 was repeated, however, 1 mg of cyclodextrin glycosyltransferase of the alkalophilic Bacillus No. 17-1 was used in place of the enzyme of Bacillus macerans. The pH of the reaction batch was set at 9. 8 g of pure cyclooctaamylose were obtained.

EXAMPLE 3

(comparison experiment) and Examples 4–10

The following standardized reaction batches were used in Examples 3-10 of the following table: 5 g of potato starch were suspended in 50 ml of buffer solution (see Example 1) and gelled. 0.5 mg of cyclodextrin glycosyltransferase of *Bacillus macerans* were employed. The reaction temperature was 50° C. Incubation times (t) in hours and crude yields of cyclooctaamylose (in % relative to the starch employed), which were achieved using particular complexing agents, are collated in the table.

TABLE

| Example | Complexing Agent | t | crude yield |
|---|---|---|---|
| 3 | Cyclododecanone | 48 | 1.5 |
| 4 | Cyclotridecanone | 42 | 42 |
| 5 | Cyclotetradec-7-en-1-one | 42 | 45 |
| 6 | Cyclohexadecane-1,9-dione | 48 | 43 |
| 7 | 9,18-Dioxatricyclo-[15.1.0.0$^{8,10}$]cyclooctadecane | 48 | 38 |
| 8 | 2,8-Dioxa-1-oxocycloheptadecane | 48 | 39 |
| 9 | 2-Oxa-1-oxocycloheptadec-7-ene | 48 | 34 |
| 10 | 2,5-Dioxa-1,6-dioxocyclohexadecane | 48 | 38 |

While only several embodiments and examples of the present invention are described, it will be obvious to those of ordinary skill in the art that many modifications may be made thereunto without departing from the spirit and scope of the invention.

What is claimed is:

1. A process for the preparation of cyclooctaamylose, comprising the step of:

enzymatically cleavaging an aqueous preparation of starch in the presence of a complexing agent, wherein as a selective complexing agent for cyclooctaamylose, a compound of the following formula (I) is employed:

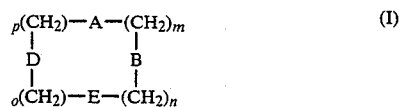

wherein,

A, B, D and E represent a substituent, independently selected from one another, selected from the group consisting of

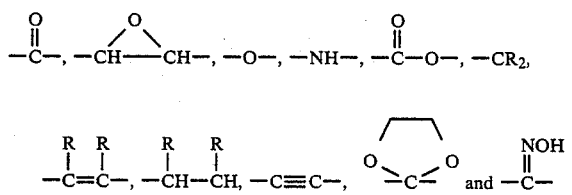

wherein,

R is a substituent selected from the group consisting of a hydrogen atom, an alkyl radical, an hydroxyl radical, an alkoxy radical and a carboxyl radical, m, n, o, p are integers each being within the range of 0 to 20, with the proviso that the number of atoms forming the ring is within the limits of 13 to 24.

2. The process according to claim 1, wherein the number of atoms forming the ring of formula (I) is within the range of 13 to 18.

3. The process according to claim 1, wherein the enzyme used in said enzymatic cleavaging step is employed in an enzyme to starch ratio of 1:2,000 to 1:50,000.

4. The process according to claim 3, wherein said enzyme to starch ratio is 1:5,000 to 1:20,000.

5. The process according to claim 1, wherein the amount of enzyme used relative to the weight of the starch employed is in the range of 1–20% by weight.

6. The process according to claim 1, wherein said aqueous preparation of starch employed has a pH in the range of 4.0 to 11.0.

7. The process according to claim 6, wherein said aqueous preparation of starch employed has a pH in the range of 6.0 to 9.5.

8. The process according to claim 1, wherein said enzymatic cleavaging step is carried out at a temperature in the range of 30°–60° C.

9. The process according to claim 8, wherein said enzymatic cleavaging step is carried out at a temperature in the range of 40°–50° C.

* * * * *